United States Patent [19]

Liff

[11] Patent Number: 4,477,430

[45] Date of Patent: * Oct. 16, 1984

[54] LIQUID BASE MAKEUP COMPOSITION

[76] Inventor: Lawrence J. Liff, 2402 E. Cheryl, Phoenix, Ariz. 85028

[*] Notice: The portion of the term of this patent subsequent to Sep. 14, 1999 has been disclaimed.

[21] Appl. No.: 404,822

[22] Filed: Aug. 3, 1982

Related U.S. Application Data

[63] Continuation-in-part of Ser. No. 111,354, Jan. 11, 1980, Pat. No. 4,349,535, which is a continuation-in-part of Ser. No. 909,576, May 25, 1978, Pat. No. 4,183,898.

[51] Int. Cl.$^3$ .................. A61K 7/021; A61K 47/00
[52] U.S. Cl. ............................. 424/63; 424/149; 424/362; 424/363
[58] Field of Search .............. 424/63, 149, 362, 363

[56] References Cited

U.S. PATENT DOCUMENTS 4,349,535  9/1982  Liff ........................................ 424/63

Primary Examiner—Dale R. Ore
Attorney, Agent, or Firm—Woodling, Krost & Rust

[57] ABSTRACT

A liquid base makeup composition primarily for use by children to simulate various things, for example, blood. This composition is relatively inexpensive and is quite safe for children's use. The composition consists essentially of about 2.0 to 3.0% cellulose; 0.2 to 0.3% quaternium-15; and the balance of the total being water. The quaternium-15 acts to keep the formulation free from unwanted bacteria and the pH of the formulation is between 7.0 and 9.5.

2 Claims, No Drawings

LIQUID BASE MAKEUP COMPOSITION

This application is a continuation-in-part of U.S. patent application Ser. No. 111,354 filed Jan. 11, 1980 and entitled "Liquid Base Makeup Composition", now U.S. Pat. No. 4,349,535, which in turn is a continuation-in-part of U.S. patent application Ser. No. 909,576, filed May 25, 1978, now U.S. Pat. No. 4,183,898, and entitled "Liquid Base Makeup Composition".

The present application discloses a liquid base makeup composition which can be used for many purposes; however, the most common use of the composition disclosed herein is for children to use as make believe blood.

The present invention discloses a composition which is ideally suited for the above mentioned purpose because it is relatively inexpensive to manufacture and therefore can be sold to the ultimate consumer at a reasonable price; it is quite realistic in appearance and when made in accordance with the present invention, it is safe for use by children whether it is accidentally taken internally or if used in its intended purpose and applied to the exterior of the body.

Historically there has always been some kind of liquid makeup used to simulate blood which was used primarily for stage purposes and in more recent years for use in movies and for television purposes. Examples of make believe blood compositions include sugar-water-base materials normally with food coloring added.

Modern technology has developed very expensive compositions to simulate the stage blood which is now used extensively in the entertainment industry. It should be kept in mind that these compositions of matter are extremely expensive and do not lend themselves to the purpose of providing an inexpensive liquid base makeup composition which can be used by children as well as others.

Children historically have used play blood of all kinds in make believe games and the number one historical product for this has been ketchup. This particular material meets one of the afore-mentioned criteria in that it is quite inexpensive; however, it lacks a realistic appearance and for that purpose is relatively unsatisfactory. Ketchup is also a food product which will spoil, develop bacteria and will cause many allergetic reactions.

Several criteria in addition to those enumerated above must be met in order to accomplish the desired end result and these include a product consistency whereby the liquid base composition will not be extremely runny and it must be easily washed off the skin or any other material that it comes in contact with. It also should not strain various fabric materials.

It is also necessary that the composition when exposed to air, start in a liquid state as a reddish-brown color and end up in the coagulated state as a brownish-red color thereby closely simulating real blood.

It is also necessary that the composition when used for the above recited purposes be essentially free of any supportive pathogenic bacteria in that it should be essentially non-toxic and safe when used either externally or if accidentally ingested.

With these thoughts in mind the present disclosure relates to a liquid base makeup composition which meets the above referred to criteria, namely it is inexpensive to manufacture and therefore is relatively inexpensive to the ultimate consumer; it is a safe material whether applied externally as it is intended or is accidentally ingested; and it is quite realistic appearing when accomplishing its intended function. The present invention as disclosed herein is relatively critical with respect to the materials which go into the composition of matter which is claimed and it is essentially critical that all of the method steps involved in making the composition be rigidly adhered to.

With the above requirements clearly in mind the basic liquid base composition which can be expanded for use in multiple makeup uses is given immediately hereinbelow. The composition has been described in connection with the making of a 600 gallon batch.

TABLE I

|  | Weight (kg) | % |
| --- | --- | --- |
| Water | 2177.3 | 96.48 |
| Hydroxypropylmethylcellulose (Methocel, 65 HG 4000) | 45.36 | 2.00 |
| Propylparaben | 1.134 | 0.05 |
| Ethylparaben | 2.268 | 0.10 |
| Chlorine dioxide 2% (Stabilized) | 30.24 | 1.34 |
| Phosphoric acid (Food grade) | 0.757 | 0.03 |
| Total | 2556.06 | 100.00 |

In the formulation given immediately hereinabove the water acts essentially as a carrier for all of the ingredients. The hydroxypropylmethylcellulose is the agent that provides a thickening of the formulation and when the composition is applied in its ultimate use, water evaporates and the thinned material which remains is the cellulose material. The cellulose material is also the bulk agent that allows the formulation to act as an adhesive.

The ethylparaben and propylparaben, the stabilized chlorine dioxide and the phosphoric acid accomplish the function of protecting the formulation from bacteria and help give it a long shelf life.

The above disclosed liquid base formulation is then normally formulated into either a red appearing makeup blood or a green appearing makeup blood, or used as a makeup adhesive to attach and/or hold cotton and/or other prosthetic devices to the face and/or other parts of the body. When being used in the last application mentioned above it may be used in an uncolored form or it may have almost any color added to it depending on the requirements of the visual effect. Also when being used in this application, when cotton is used, this liquid base makeup formulation can be applied over the cotton to help shape it. This causes the cotton to become firm once the water has evaporated from the formulation. When the formulation is colored and used in this way it becomes a regular makeup base. In order to accomplish this, various artificial colorants are added to each 600 gallon batch of the liquid base formulation. The amounts, color blends, and intensities of these added dyes are determined by the intended end use for that 600 gallon batch of liquid base makeup composition. The color standards for these dye materials are set by the World Health Organization. These colors are listed in the Code of Federal Regulations, Title 21, Parts 1–9. The amount of colorant used is on the order of 0.1% (0.001) of the total batch weight.

The basic liquid formulation is comprised of the water, cellulose material, propylparaben, ethylparaben, stabilized chlorine dioxide and food grade phosphoric acid in the amounts indicated. If a red blood effect is desired, it is only necessary to incorporate into the basic liquid formulation red colorant materials for the red blood and if a green blood effect is desired, green colorant materials are added and the red materials are omitted from the basic liquid formulation.

It has been found that the pH level for the liquid base formulation which is most conducive to long shelf life and lack of bacterial contamination is a pH of about 5.0 to 6.0 and preferably 5.5. The water which is used in the formulation is normally tap water (not sterile) which varies substantially in its chemical and bacterial makeup as introduced into the formulation. Another factor which affects the formulation is the amount of coloring material which is added. The preservative system used in this disclosure varies as a function of the above. As a result of these variations the amount of ethylparaben and propylparaben may vary from 0 to 0.15% and the phosphoric acid may vary from 0 to 0.03%.

To illustrate the above, the pH of the tap water used in combination with the chlorine dioxide may result in a pH for the system of just about 5.5 and if this is the case, the phosphoric acid is omitted. If the pH is above 5.5 then an appropriate amount of phosphoric acid is added to reduce the pH to preferably 5.5.

In like fashion if the formulation is found to contain pathogenic bacteria it is necessary that an appropriate amount of ethylparaben and propylparaben (in the indicated range), be added until all trace of pathogens disappear. If pathogens are not detected in the formulation then it is not necessary to add the ethylparaben and propylparaben.

The blood makeup composition enumerated hereinabove uniquely satisfies the criteria for a satisfactory product in that the material when utilized has a consistency closely approximately actual blood thereby giving a realistic effect when used. Because of the relatively inexpensive ingredients it can be sold to the ultimate consumers (usually children) at a relatively inexpensive price. Also because of the ingredients that go into this unique composition it is non-toxic and as a result it is not harmful when used either in its intended purpose externally or in the event the composition is accidentally ingested.

The method steps that are involved in making the liquid base makeup composition are extremely important and critical and if altered even in the slightest manner the formulation will be either too thick or too thin. It is also possible, if the following steps are not strictly adhered to, that the formulation may lose its bacteriological protection altogether.

The method steps that are involved in the making of the liquid base makeup composition are given hereinbelow.

1. Clean, disinfect and rinse all mixing equipment.
2. Place 132.3 Kg. of 180° F. water into a mixing container.
3. Add all ethylparaben and propylparaben and agitate for 5 minutes.
4. Add all phosphoric acid and 11.34 Kg. stabilized chlorine dioxide and agitate for 10 minutes.
5. Add all dye and colorant materials and agitate 10 minutes.
6. Continue agitation and begin to add 226.8 Kg. 180° F. water and slowly add the hydroxypropylmethylcellulose at the same time.
7. Let solution agitate for about 15 minutes.
8. Add 1,818.2 Kg. of cold water and continue to agitate.
9. Add 11.34 Kg. of stabilized chlorine dioxide and agitate approximately 2 hours.
10. Add 7.56 Kg. of stabilized chlorine dioxide approximately 10-16 hours after completing step #9 and agitate 2-3 hours.
11. Agitate periodically as long as the composition remains in the mixing container.

As stated, it is necessary to follow the method steps critically and to the letter otherwise the criteria enumerated hereinabove for a satisfactory liquid base composition will not be achieved.

It will be apparent from the above that the formulation is acidic in its composition. The preservatives are very powerful and effective in keeping the formulation free from unwanted bacteria; however, there is some difficulty in maintaining the stability of the composition. The chlorine dioxide is the most difficult element to handle and often affects the color system by reacting almost like a bleach.

It has been found that an effective formulation under the present teachings can be produced by using quaternium-15 to replace both parabens, the stabilized chlorine dioxide, and the food grade phosphoric acid.

One of the advantages of using quaternium-15 is that it operates in a base solution. The previously described systems operate in an acid solution in reference to the pH level of the formula. This is a particularly important development since an acid solution tends to be more irritating to the skin than a base solution.

Another advantage is that four chemicals are being replaced with one chemical. Again, this simplifies the formulation and cuts down the possibilities of skin reactions. People tend to be sensitive to one chemical or perhaps a combination of chemicals when used together. By replacing four chemicals with one the probability for problems is greatly reduced.

It has been discovered that the quaternium-15 should be added to the water and hydroxypropylmethylcellulous mixture in a weight percentage amount of from 0.2% to 0.3% based upon the total formulation weight. The hydroxypropylmethylcellulose is present in an amount of about 2.0 to 3.0% and the balance of the formulation is water. Coloring materials are added but in very small amounts.

The amount of quaternium-15 used varies depending on the amount of hydroxypropylmethylcellulous used. If the formulation contains more hydroxypropylmethylcellulose, i.e., an amount near the 3% level, the quaternium-15 must be increased to something approaching the 0.3% limit. Likewise, if the hydroxypropylmethylcellulose is around the 2% level, then the quaternium-15 is usually at near the 0.2% level.

The water used in the formulation is normally tap water which has a pH of about 6.9 to 7.5 and the addition of the quaternium-15 brings the pH normally in the range of 8 to 9.5. The pH should not be above 10 and usually is above 7. The amount of quaternium-15 used is in the 0.2 to 0.3% range in the above considerations.

Another advantage of the use of the quaternium-15 is that the mixing of the formulation can be without heat, i.e., with water directly from the tap. While the quaternium-15 is usually dissolved in a small amount of water and then added to the main body of water, hydroxypropylmethylcellulous and coloring material, it can be directly added to the main body of water. Agitation is provided to properly mix the materials together.

Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A liquid base formulation for multiple makeup uses consisting of about 2.0 to 3.0% cellulous; 0.2 to 0.3% quaternium-15; and the balance of the total being water; said percentages being by weight and based upon the total formulation weight; said quaternium-15 acting to keep the formulation free from unwanted bacteria; the pH of the formulation being between 7.0 and 9.5.

2. A liquid base formulation as claimed in claim 1 wherein the cellulose is hydroxypropylmethylcellulose.

* * * * *